(12) United States Patent
Lin

(10) Patent No.: US 6,846,297 B2
(45) Date of Patent: Jan. 25, 2005

(54) MEDICINAL GERMFREE DRY SMEARING PIECE ATTACHED ON A SHELL CONTAINING GERMFREE MEDICINAL SOLUTION

(76) Inventor: Chung Sing Lin, No. 33-1, Ta Chiao 3rd Street, Yung Kang Shih, Tainan Hsien (TW)

( * ) Notice: Subject to any disclaimer, the term of this patent is extended or adjusted under 35 U.S.C. 154(b) by 0 days.

(21) Appl. No.: 10/356,538

(22) Filed: Feb. 3, 2003

(65) Prior Publication Data

US 2004/0153022 A1 Aug. 5, 2004

(30) Foreign Application Priority Data

Feb. 8, 2002 (TW) ........................................ 91102352 A

(51) Int. Cl.[7] ............................................ A61M 35/00
(52) U.S. Cl. .................... 604/1; 604/2; 604/3; 604/4
(58) Field of Search .................................. 604/1, 2, 3, 4

(56) References Cited

U.S. PATENT DOCUMENTS

| 4,430,013 A | * | 2/1984 | Kaufman | 401/132 |
| 5,762,494 A | * | 6/1998 | Archambault | 433/80 |
| 6,371,675 B1 | * | 4/2002 | Hoang et al. | 401/205 |

* cited by examiner

*Primary Examiner*—Jacqueline Stephens
(74) *Attorney, Agent, or Firm*—Bacon & Thomas

(57) ABSTRACT

A medicinal germfree dry smearing piece attached on a shell containing germfree medicinal solutions includes a smearing piece and a shell for containing germfree medicinal solutions. The smearing piece is attached on an intermediate portion of the shell where an easily bent neck is formed. In using, the shell is bent into two halves and folded on each other to make the neck crack open to let the solutions in the shell to flow out and at once absorbed by the smearing piece to be used for swabbing on a wound or the like. Thus the smearing piece with the shell not yet used can be carried out conveniently in a hygienic condition and with safety in use.

12 Claims, 7 Drawing Sheets

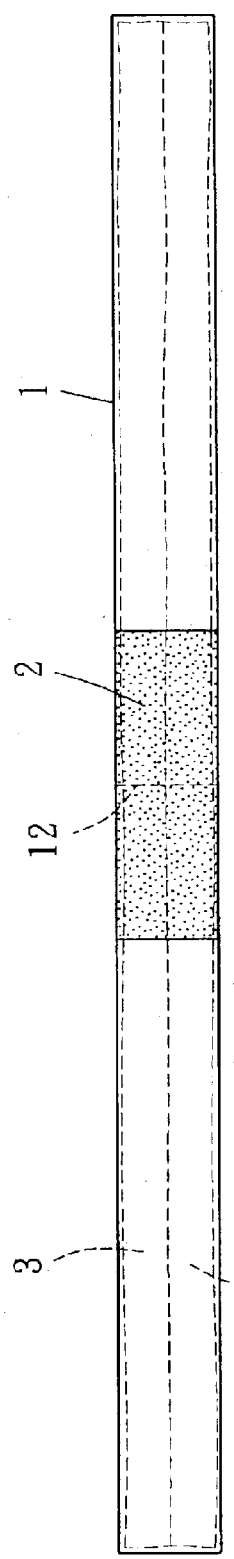
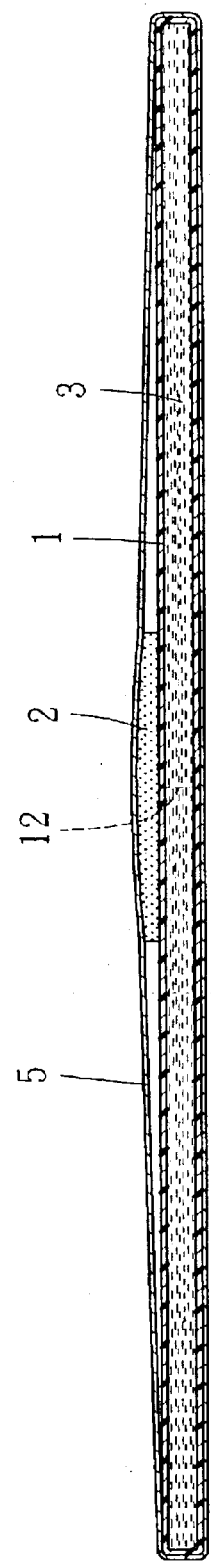

US 6,846,297 B2

MEDICINAL GERMFREE DRY SMEARING PIECE ATTACHED ON A SHELL CONTAINING GERMFREE MEDICINAL SOLUTION

BACKGROUND OF THE INVENTION

This invention relates to a medicinal germfree dry smearing piece attached on a shell containing germfree medicinal solutions, particularly to one attached on an intermediate portion of an shell, different from a conventional smearing piece such as cotton swabs with cotton wound on the top. Further, the smearing piece after used can present a discernible shape of "already used" so that a user is forced to take action to throw it away, preventing the used one from being used again and establishing precise hygienic notion.

Generally, conventional medicinal smearing pieces such as cotton swabs are to be smeared with some sterilizing solution to carry out cleansing or sterilizing work. Chances are that some external matters may fall into a bottle filled with medicinal solution to pollute the solution. If the conventional smearing pieces are to be used outdoors, bottles filled with medicinal solutions have to be carried out, not convenient to use them.

Further, in the process of smearing medicinal solution or cream, cans or bottles filled with them have to be frequently opened and closed, or opened for a quite long period of time, possible to permit bacteria or germ or miscellaneous matters to fall in the cans or bottles to become polluted. Besides, doctors or nurses may sometimes use not sterilized tweezers to pinch cotton and insert in a can or bottle for smearing medical solution or cream again and again, The it means that substantive amount of bacteria or germ may go into the can or bottle, potentially causing serious results. In case more than two kinds of medical solutions or creams are to be used for swabbing a wound, the same tweezers may be used to cause bad results. Or after used the same tweezers may be used for pinching cotton again without proper sterilization and inserting in a can or bottle for smearing another medical solution or cream. Then two kinds of medical solutions or creams may be mixed together, which may occur to professional medical persons, and common laymen as well. Especially women often are not so careful to use cotton for smearing properly during a menstruation period, resulting in an accidental contract of a disease.

As for packing of cotton swabs, they have an upper end or a lower end or the both ends wound with cotton and if they are all packed with the cottoned ends upward, in taking out action polluted matters and bacteria on fingers may attach on the cottoned ends to pollute them to some extent, and continual action of taking out the cotton swabs may add up chances of pollution of the cotton swabs. If cotton swabs have a lower end wound with cotton, and are packed with the lower ends packed downward, the cotton ends contact the bottom surface of a can or container, and then dirt or bacteria stuck on the bottom may gradually increase, as the can is opened and closed again and again, and then cottoned ends may gradually be attached with dirt and bacteria. Thus the conventional packing modes are not ideal. In addition, there are also cotton swabs, which has medical solution contained in a shank portion, with one of them being open and with the other ends closed. When they are to be used, the closed end is to be cut open to let the solution automatically flow to the cotton due to capillary action. However, this kind of cotton swab may have a disadvantage that solution may be insufficient or automatically flow to the cotton before it is used.

In addition to medicinal treatment, two kinds of medicines may be used for producing a certain effect such as hair dying in out daily life, that is, a kind of chemical change is produced by mixing together two kinds of medicines for immediate use owing to impossibility of long-term preservation. And the kinds of medicines are separately kept until they are to be mixed for use, so a user may feel troublesome and inconvenient.

SUMMARY OF THE INVENTION

The invention has been devised with a purpose of offering a medicinal germfree dry smearing piece attached on a shell with germfree medicinal solutions, convenient to carry along and highly hygienic and safe to use.

Another purpose is to offer a medicinal germfree dry smearing piece attached on a shell containing germfree medicinal solutions, with different medicinal solutions separately sealed completely in the shell and possible to be opened at the same time so as to merge together and flow to the smearing piece made of absorbing material to be absorbed and then swabbing on a wound of a person. Further, a user can discern the smearing piece already used or not yet used by the change of its outward structure so as to totally prevent the used one from used once again to cause danger of contracting of disease, and to establish correct hygienic idea.

The feature of the invention is a shell for containing some medicinal germfree solutions separately and having a thin neck formed on an intermediate portion of the shell and easily bent to broken into two halves and folded on each other, and a smearing piece made of sbsorbing and flexible material attached on the neck. Then in use, the shell is to be bent into two halves and folded on each other to form a grip easily gripped, with the medicinal solutions flowing out to the smearing piece, which then at once absorbs to have the medicinal solutions and ready for use.

BRIEF DESCRIPTION OF DRAWINGS

This invention will be better under stood by referring to the accompanying drawings, wherein:

FIG. 2 is an upper view of a first embodiment of a medicinal germfree dry smearing piece attached on a shell containing germfree medicinal solutions in the present invention;

FIG. 4 is a side view of the medicinal germfree dry smearing piece attached on a shell containing medicinal solutions in the present invention, showing the sealed condition of the medicinal solutions in the shell;

DETAILED DESCRIPTION OF THE PREFERRED EMBODIMENTS

Figure 1:
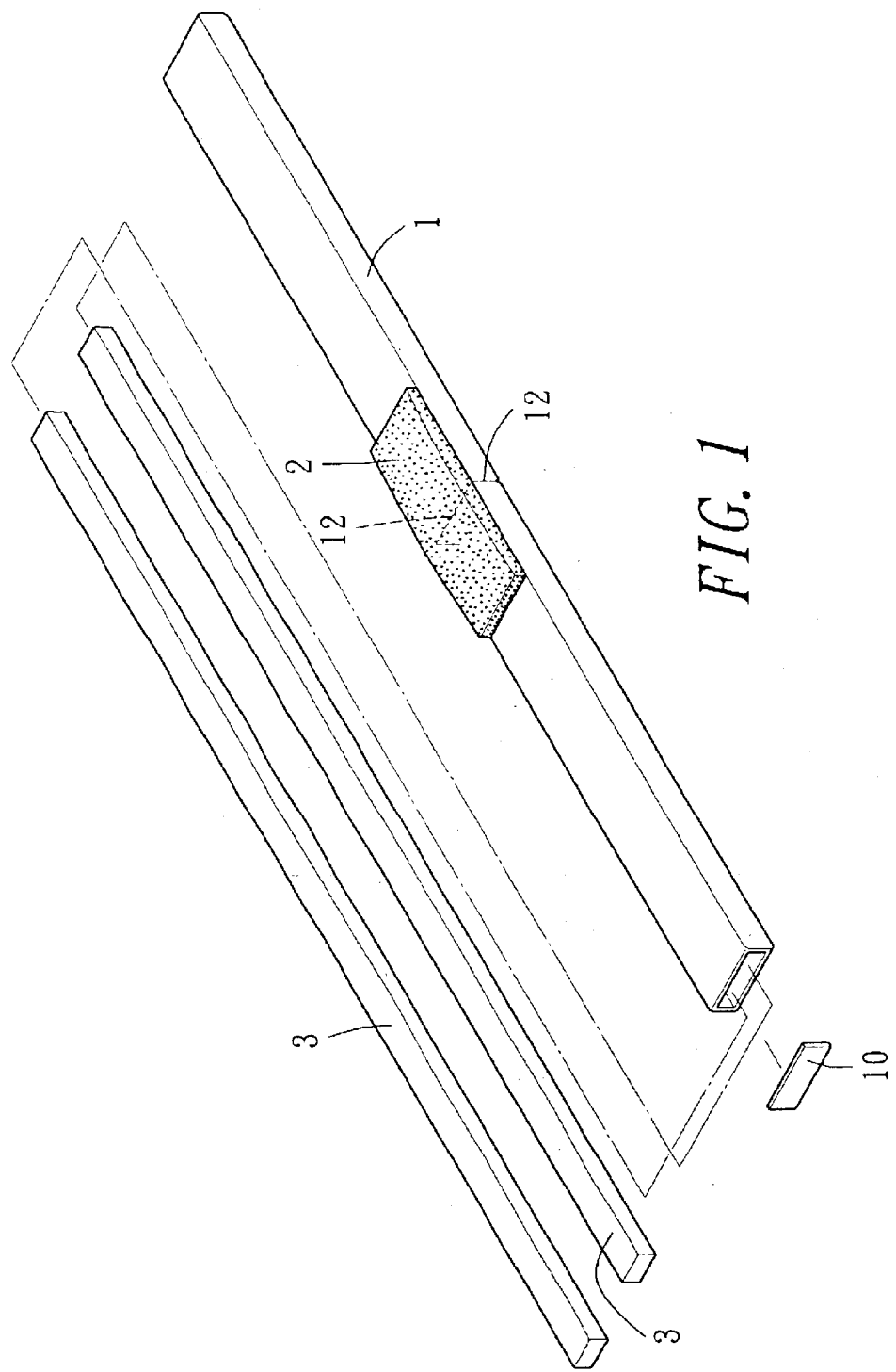
FIG. 1 is an exploded perspective view of a medicinal germfree dry smearing piece attached on a shell containing medicinal solutions in the present invention.

A first embodiment of a medicinal germfree dry smearing piece attached to a shell containing germfree medicinal solutions in the present invention, as shown in FIGS. 1 and 2, includes a shell 1 having an elongate empty interior and a smearing piece 2 as main components.

The shell 1 has a thinner neck 12 than the rest portion formed in an intermediate portion, and a plurality of separate capsules 3 placed lengthwise side by side in the interior for containing medicinal solutions. The shell 1 has two opposite ends closed up with a cap 10, made of transparent material so as to let the contents of the capsule visible from outside.

The smearing piece 2 is made of easily absorbing and flexible material such as cotton, technical fabric, or the like, attached on the neck 12 of the shell 1.

Figure 3:
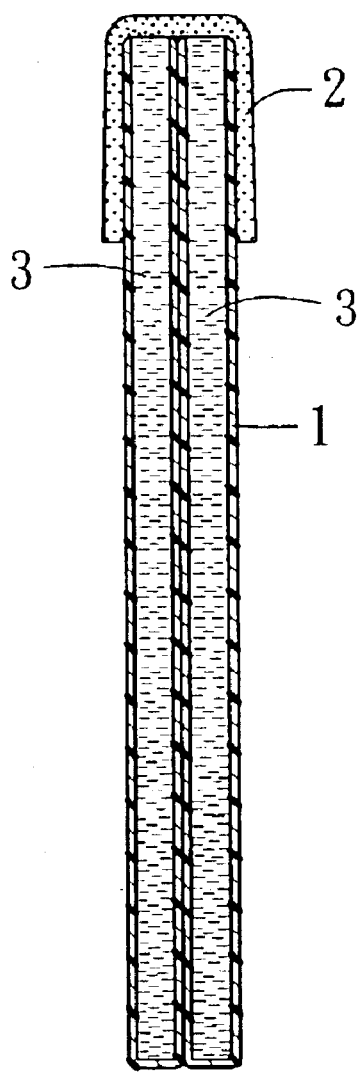
FIG. 3 is a side view of the medicinal germfree dry smearing piece attached on a shell containing germfree medicinal solutions in the present invention, showing the shell bent to use the smearing piece.
Figure 7:
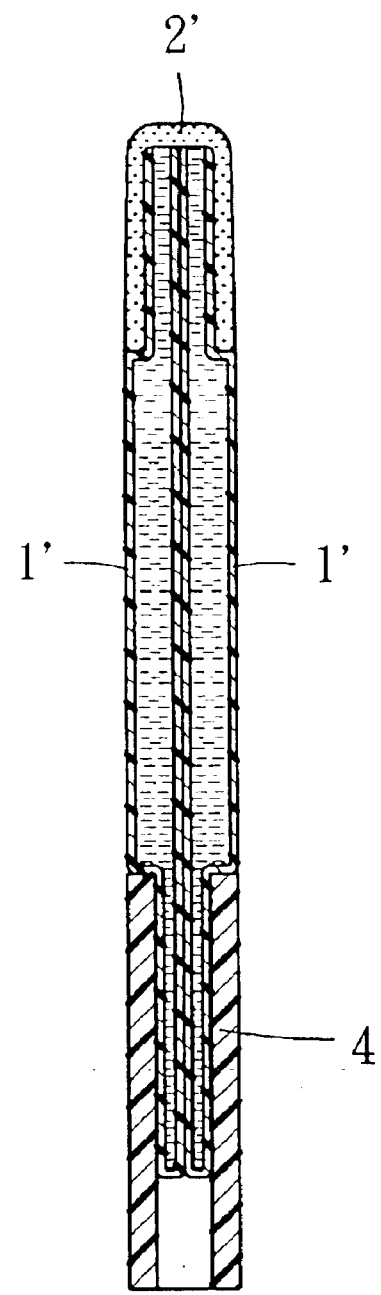
FIG. 7 is a side view of the second embodiment of a medicinal germfree dry smearing piece attached on a shell germ free medicinal solutions in the present invention, showing the shell bent to use the smearing piece.
Figure 5:
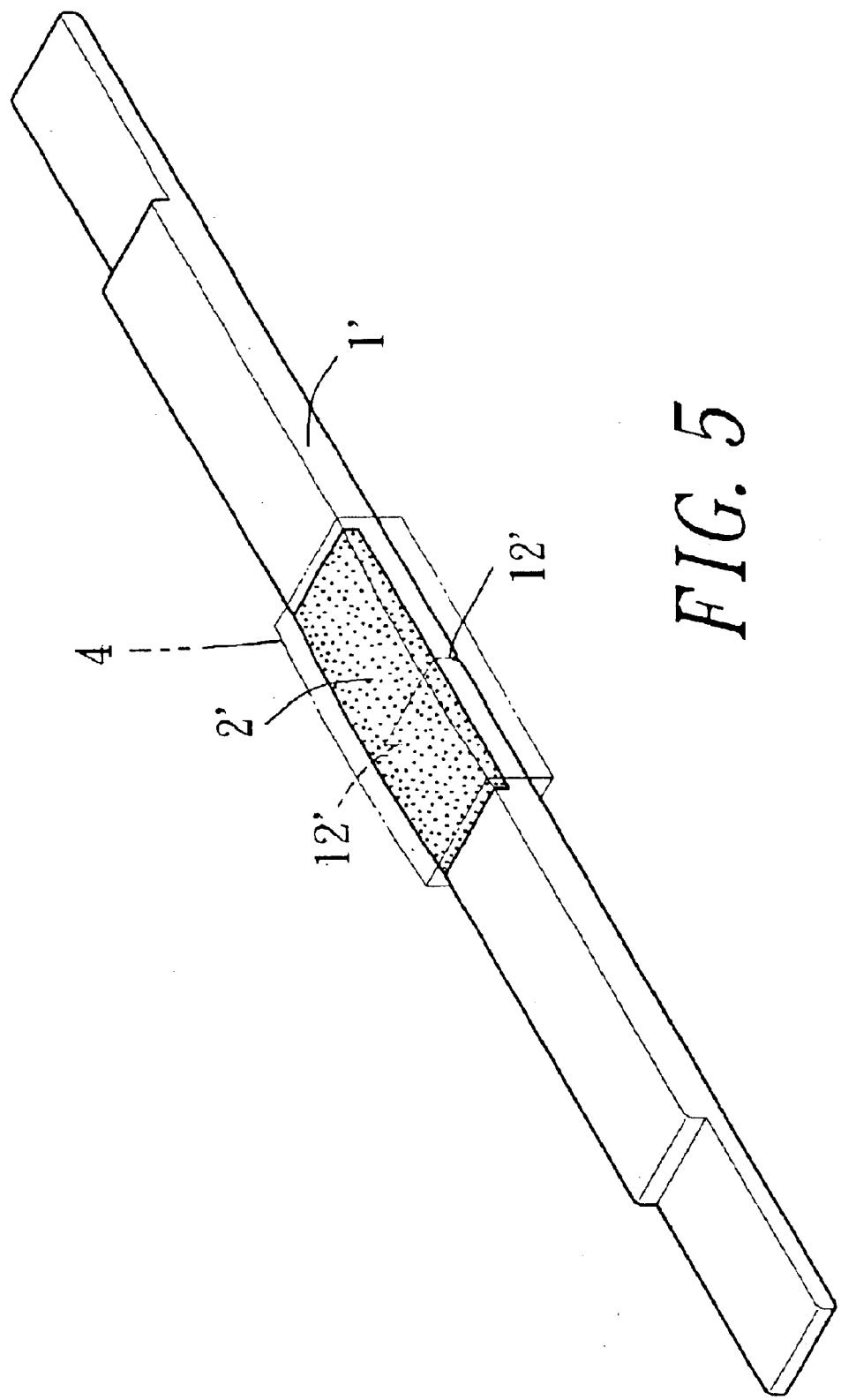
FIG. 5 is a perspective view of a second embodiment of a medicinal germfree dry smearing piece attached on a shell germfree medicinal solutions in the present invention.
Figure 6:
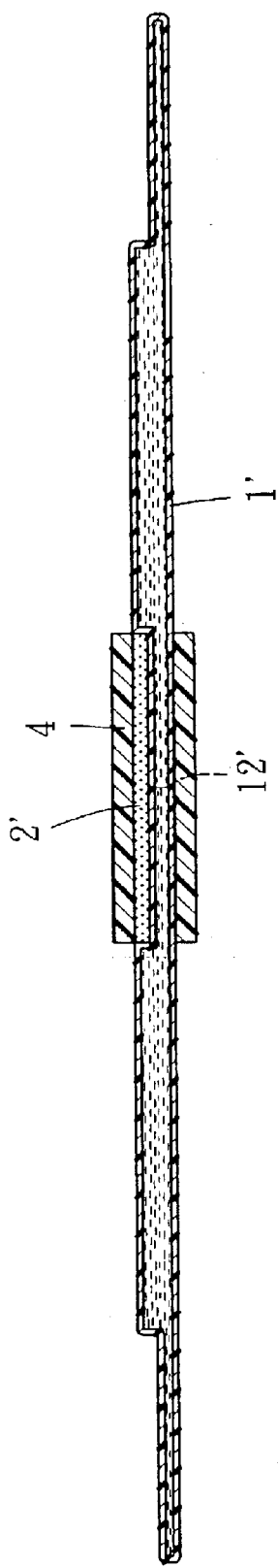
FIG. 6 is a side view of the second embodiment of a medicinal germfree dry smearing piece attached on a shell containing germfree medicinal solutions in the present invention.
Figure 8:
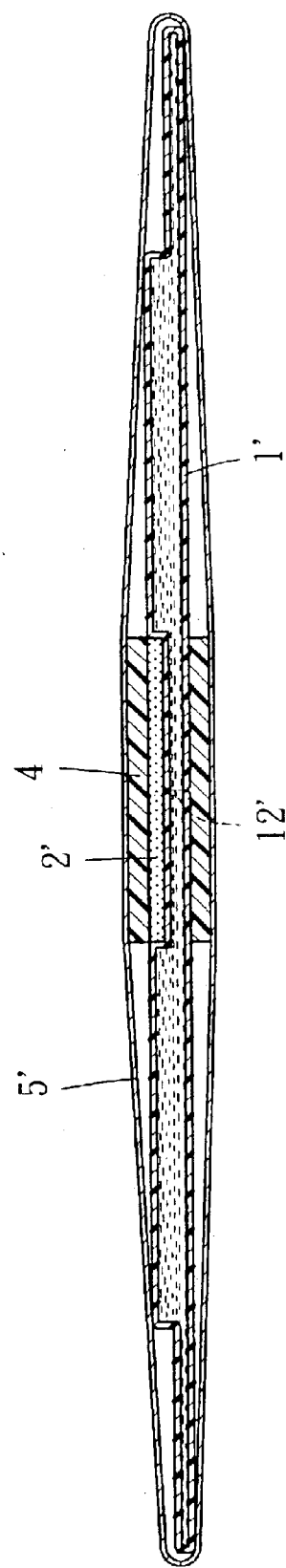
FIG. 8 is a side view of the second embodiment of a medicinal germfree dry smearing piece attached on a shell containing germfree medicinal solutions, showing the solutions sealed in the shell.
Figure 9:
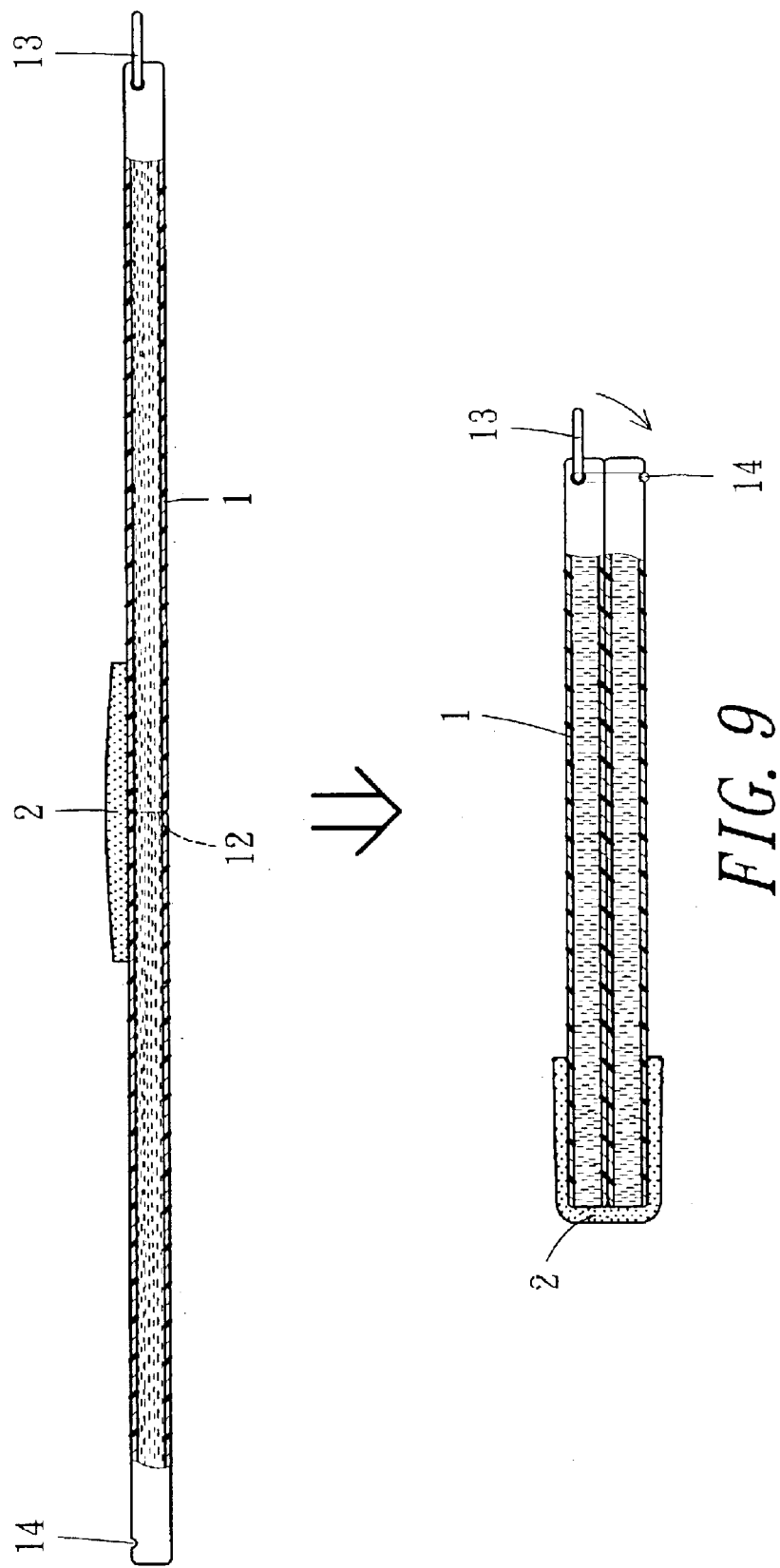
FIG. 9 is a side view of a third embodiment of a medicinal germfree dry smearing piece attached on a shell containing germfree medicinal solutions, showing the shell bent to use the smearing piece; and, FIG. 10 is a side view of a medicinal germfree dry smearing piece attached on a shell containing germfree medicinal solutions in the present invention, showing the shell being bent to use the smearing piece.
Figure 10:
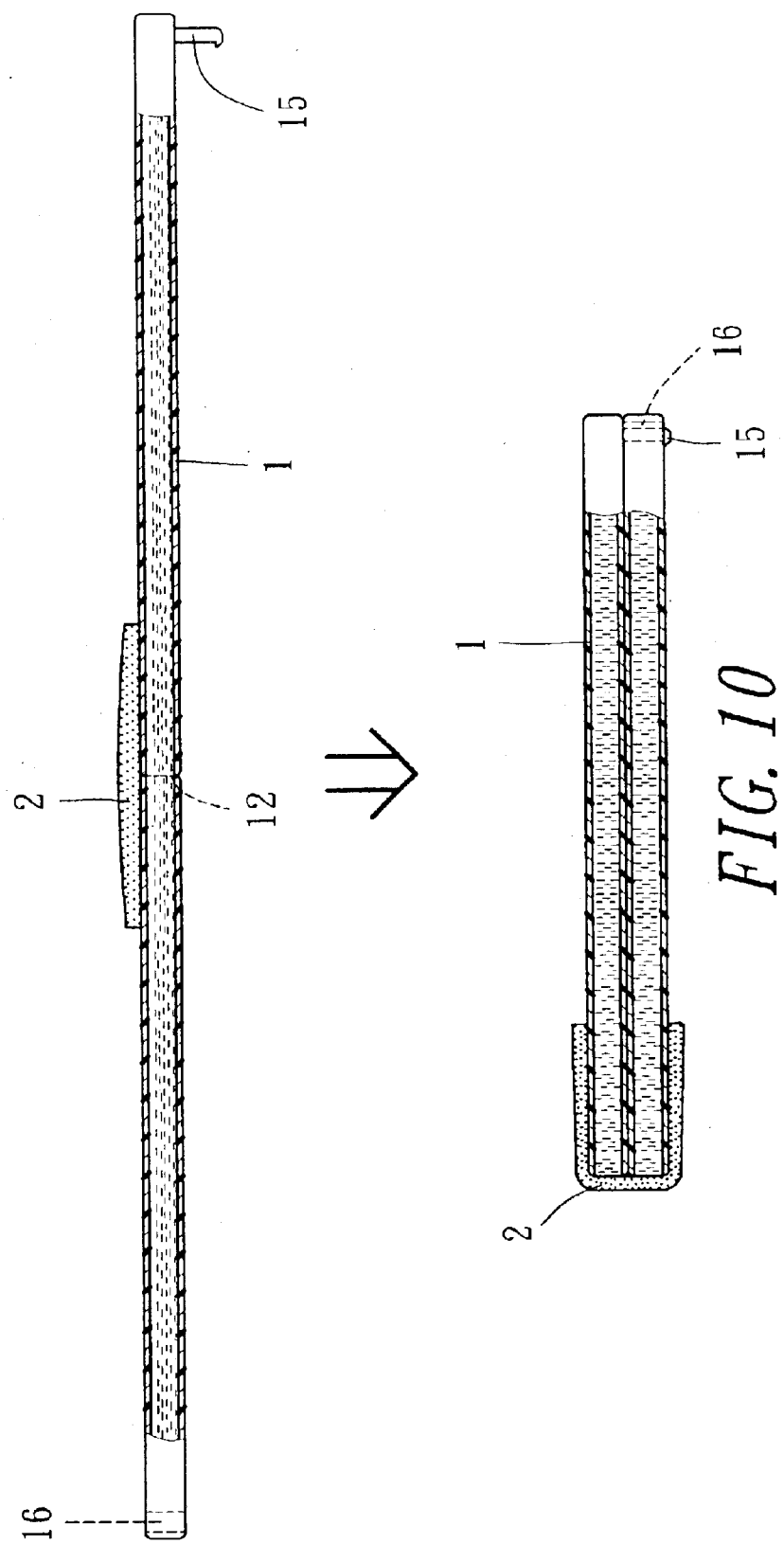

In using the smearing piece, a user grips the two ends of the shell 1 and bends it with the neck 12 as a bending point to break completely the upper side of the shell 1 and the lower side bent but not completely broke off, and with the capsules containing the medicinal solutions also broken as shown in FIG. 3. Then the medicinal solutions in the capsules 3 may flow out from the broken neck to the smearing piece 2, which at once absorbs the medicinal solutions into itself. Then the user may grips the folded up shell 1 as a grip, and the smearing piece may be stretched to completely wrap up the broken neck of the shell 1 due to its flexibility. Then the user can swab the smearing piece 1 wet with the solutions to a wound for sterilizing, cleaning or treating.

Therefore, this smearing piece is very handy to be carried along and simple and safe to use, with the medicinal solutions never contact outer air to keep hygienic safety.

Moreover, as shown in FIG. 4, a plastic bag 5 may be used to wrap up the whole smearing piece 2 with the shell 1, after the capsules 3 are placed in the shell 1 and closed up the ends with the covers 10 in a germfree condition. Then the smearing piece 2 with the shell 1 is kept quite clean and hygienic, and a user only tears open the plastic bag 5, grips the two ends of the shell 1 and bends it into two halves and folded on each other, with the smearing piece 2 stretched to wrap the broken and open neck 12. Meanwhile the medicinal solutions may flow out from the capsules 3 to the smearing piece 2, which can at once absorb them to become wet, ready to be used for medical treatment. After use, it may be discarded, without possibility of reusing it to cause danger. Besides, the plastic bag 5 can have its surface printed with the name of the medicinal solutions and its using method for a user to read so as to avoid misuse.

The shell 1 in the invention is mainly for containing medicinal solutions, so small tubes for filling medicinal solutions can be also used instead of the capsules 3, to obtain the same function. Or the shell 1 can be made to have a plurality of separate lengthwise chambers for directly filling medicinal solutions and the ends can be sealed. Or it is possible to make the shell 1 provided with a plurality of lengthwise separate chambers with one of them not filled with solution, letting two not abutting chambers filled with solution so as to separate them completely. For example, there are three chambers in the shell 1, with the middle one not filled with solution and with the rest two chambers filled with solution, with the other two chambers with solution completely separated from each other. Any modification of the shell 1 may be covered in the claim of the invention.

The medicinal germfree dry smearing piece attached on a shell containing medicinal solutions in the invention has the following effects and advantages.

1. It offers a handy operation for a user, who needs two or more kinds of medicinal solutions for medical treatment, possible to instantly obtain effective use.

2. It shortens to a half of the original length after used with the shell bent into two halves and folded on each other, changing greatly its outer structure to be recognized as "already used" to force a user to discard it after used, preventing it from being used repeatedly.

3. It can be used by fingers to directly bend the shell into two halves without using any thing or tool, letting the medicinal solutions instantly flow to the smearing piece for use, having timeliness, easy handling, convenience and safety.

4. The smearing piece is located on the intermediate portion of the shell, and not to be dirtied in a packed condition as "conventional cotton swabs packed with cottoned ends upward or downward".

5. As the smearing piece located in the intermediate portion of the shell and the rest portions are all wrapped with a protective plastic bag, the smearing piece and the easily bent neck as well are effectively kept clean, preventing the shell from bent off accidentally.

While the preferred embodiments of the invention have been described above, it will be recognized and understood that various modifications may be made therein and the appended claims are intended to cover all such modifications that may fall in the spirit and scope of the invention.

What is claimed is:

1. A medicinal germfree dry smearing piece attached on a shell comprising an elongated shell and a smearing piece, said shell having an elongated empty interior for at least one solution and an easily bent thin neck formed in an intermediate portion of said shell to allow bending of the elongated shell at said thin neck into two halves back on each other to form a handle and with release of said solution into said smearing piece, said smearing piece comprising a material firmly attached on said thin neck for absorbing released solution, and wherein a clamping member is provided to clamp said handle in place.

2. The medicinal germfree dry smearing piece attached on a shell claimed in claim 1, wherein said shell contains within the empty interior a sterilizing solution, a medicinal solution or a cleaning solution.

3. The medicinal germfree dry smearing piece attached on a shell containing germfree medicinal solutions as claimed in claim 2, wherein said shell has a single empty interior for a single solution to be filled therein.

4. The medicinal germfree dry smearing piece attached on a shell containing germfree medicinal solutions as claimed in claim 2, wherein solutions to be filled in said shell are in advance filled in capsules and then placed in said empty interior of said shell.

5. The medicinal germfree dry smearing piece attached on a shell as claimed in claim 1 or 2, wherein said shell is made of transparent material to enable any solution therein to be visible from outside the shell.

6. The medicinal germfree dry smearing piece attached on a shell as claimed in claim 1, wherein said smearing piece is made of easily-absorbing-liquid material.

7. The medicinal germfree dry smearing piece attached on a shell containing germfree medicinal solutions as claimed in claim 6, wherein the easily-absorbing-liquid material is cotton or technical fabric.

8. The medicinal germfree dry smearing piece attached on a shell containing germfree medicinal solutions claimed in claim 1, wherein said smearing piece contains a cover.

9. The medicinal germfree dry smearing piece attached on a shell as claimed in claim 8, wherein said cover is removable and forms said clamping member.

10. The medicinal germfree dry smearing piece attached on a shell claim 1, wherein said smearing piece attached on said shell is wholly enclosed in a plastic bag.

11. The medicinal germfree dry smearing piece attached on shell in claim 1, wherein said clamping member comprises a clamping ring formed at one end of said shell and a shallow annular groove formed in the other end of said shell, so said clamping ring engages with said shallow annular groove for clamping the grip formed by said shell after said shell is bent into two halves and then folded on each other.

12. The medicinal germfree dry smearing piece attached on a shell containing germfree medicinal solutions as claimed in claim 1, wherein the clamping member comprises a projection formed at one end of said shell and a through hole formed in the other end of said shell, said projection engaging with said through hole in case of said shell is bent into two halves and folded on each other to become the grip.

* * * * *